US010934538B2

(12) United States Patent
Lee

(10) Patent No.: US 10,934,538 B2
(45) Date of Patent: Mar. 2, 2021

(54) 3D-PRINTED MINIATURE BIOLOGICAL CONSTRUCTS

(71) Applicant: Cleveland State University, Cleveland, OH (US)

(72) Inventor: Moo-Yeal Lee, Pepper Pike, OH (US)

(73) Assignee: Cleveland State University, Cleveland, OH (US)

(*) Notice: Subject to any disclaimer, the term of this patent is extended or adjusted under 35 U.S.C. 154(b) by 182 days.

(21) Appl. No.: 15/404,291

(22) Filed: Jan. 12, 2017

(65) Prior Publication Data

US 2017/0198275 A1 Jul. 13, 2017

Related U.S. Application Data

(60) Provisional application No. 62/277,592, filed on Jan. 12, 2016.

(51) Int. Cl.
| | | |
|---|---|---|
| *C12N 11/04* | (2006.01) | |
| *G01N 33/50* | (2006.01) | |
| *C12N 5/071* | (2010.01) | |
| *C12Q 1/02* | (2006.01) | |

(52) U.S. Cl.
CPC ............ *C12N 11/04* (2013.01); *C12N 5/0671* (2013.01); *C12Q 1/02* (2013.01); *G01N 33/5005* (2013.01); *C12N 2513/00* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 9,097,702 | B2 | 8/2015 | Fischbach |
| 9,133,429 | B2 | 9/2015 | Higuera et al. |
| 9,481,868 | B2 | 11/2016 | Nguyen et al. |
| 2004/0197236 | A1* | 10/2004 | Vanmaele ............ B01J 19/0046 506/39 |
| 2009/0263849 | A1 | 10/2009 | Sun et al. |
| 2011/0190162 | A1 | 8/2011 | Lee et al. |
| 2011/0212501 | A1 | 9/2011 | Yoo |
| 2011/0259742 | A1* | 10/2011 | Li ..................... B01L 3/502784 204/451 |
| 2012/0088693 | A1 | 4/2012 | Lee et al. |
| 2012/0165224 | A1 | 6/2012 | Song et al. |
| 2013/0174287 | A1* | 7/2013 | Higuera ................ B01L 3/5085 800/8 |
| 2014/0045256 | A1 | 2/2014 | Lee et al. |
| 2014/0154722 | A1 | 6/2014 | Yeal et al. |
| 2014/0227145 | A1 | 8/2014 | Kim et al. |
| 2014/0273053 | A1 | 9/2014 | Lee et al. |
| 2014/0287960 | A1 | 9/2014 | Shepard et al. |
| 2015/0282885 | A1 | 10/2015 | King et al. |
| 2016/0074558 | A1 | 3/2016 | Murphy et al. |
| 2016/0122723 | A1 | 5/2016 | Retting et al. |
| 2016/0348049 | A1* | 12/2016 | Baba ..................... C12M 23/20 |

FOREIGN PATENT DOCUMENTS

| | | |
|---|---|---|
| CN | 103930066 | 7/2014 |
| CN | 104717987 | 6/2015 |
| KR | 20140072883 | 6/2014 |
| KR | 201600336619 | 4/2016 |
| WO | 2001007891 | 2/2001 |
| WO | 2007053561 | 5/2007 |
| WO | 2012125906 | 9/2012 |
| WO | 2012158875 | 11/2012 |

OTHER PUBLICATIONS

International Search Report and Written Opinion from PCT/US17/013144 dated Mar. 30, 2017.
Lee, D.W. et al., "Automatic 3D Cell Analysis in High-Throughput Microarray Using Micropillar and Microwell Chips," Journal of Biomolecular Screening, 2015, 1178-1184, Society for Laboratory Automation and Screening.
Kwon, S.J. et al., "High-throughput and combinatorial gene expression on a chip for metabolism-induced toxicology screening," Nature Communications, May 6, 2014, 5:3739, DOI 10.1038/ncomms4739, 2014 Macmillan Publ. Ltd.
Lee, D.W. et al., "High-Throughput Screening (HTS) of Anticancer Drug Efficacy on a Micropillar/Microwell Chip Platform," Analytical Chemistry, 2014, 86(1), 535-542, ACS Publications.
Lee, D.W. et al., "Application of the DataChip/MetaChip technology for the evaluation of ajoene toxicity in vitro," Archives of Toxicology, 88(2), 283-290, Jul. 28, 2013 Springer.
Lee, D.W. et al., "Plastic pillar inserts for three-dimensional (3D) cell cultures in 96-well plates," Sensors and Actuators B, 177(1), 2013, 78-85, Elsevier B.V.
Zhang, H.Y. et al., "High-Throughput Transfection of Interfering RNA into a 3D Cell-Culture Chip," Small, 8(13), 2091-2098, Jul. 2012.
Fernandez, T.G. et al., "Three-Dimensional Cell Culture Microarray for High-Throughput Studies of Stem Cell Fate," Biotechnology and Bioengineering, vol. 106, No. 1, 106-118, May 1, 2010.
Park, T.J., et al., "Signal Amplification of Target Protein on Heparin Glycan Microarray," Analytical Biochemistry, 383, 116-121, Dec. 1, 2008.
Fernandes, T.G. et al., "On-Chip, Cell-Based Microarray Immunofluorescence Assay for High-Throughput Analysis of Target Proteins," Analytical Chemistry, 80, 6633-6639, Sep. 1, 2008.
Lee, M.Y. et al, "Three-dimensional cellular microarray for high-throughput toxicology assays," Proc. of the Nat'l. Academy of Sciences (PNAS), 105(1), 59-63, Jan. 8, 2008.

(Continued)

*Primary Examiner* — Blaine Lankford
(74) *Attorney, Agent, or Firm* — Calfee, Halter & Griswold LLP

(57) ABSTRACT

A method of creating a miniature multicellular biological construct and a method for studying cellular environments using the miniature multicellular biological construct is provided. The method for making the miniature multicellular biological construct includes suspending cells in a hydrogel, depositing the cell-suspension into a microwell, gelling the cell-suspension, and incubating the cell-suspension. The method for studying cellular environments includes imaging the miniature multicellular biological construct.

7 Claims, 4 Drawing Sheets

(56) References Cited

OTHER PUBLICATIONS

Kwon, S.J. et al., "High-Throughput, Microarray-Based Synthesis of Natural Product Analogues via in vitro Metabolic Pathway Construction," ACS Chemical Biology, 2(6), 419-425, May 25, 2007.
Lee, M.Y. et al., "Human P450 Microarrays for In Vitro Toxicity Analysis: Toward Complete Automation of Human Toxicology Screening," Journal of the Assn. for Lab. Automation, 11(6), 374-380, Dec. 2006.
Lee, M.Y. et al., "Metabolizing enzyme toxicology assay chip (MetaChip) for high-throughput microscale toxicity analyses," Proc. of the Nat'l. Academy of Sciences (PNAS), 102(4), 983-987, Jan. 25, 2005.
Lee, D.W. et al., "High-Throughput, Miniaturized Clonogenic Analysis of a Limiting Dilution Assay on a Micropillar/Microwell Chip with Brain Tumor Cells," Small, 10(24), 5098-5105, 2014 Wiley-VCH Verlag GmbH & Go. KGaA, Weinheim.

\* cited by examiner

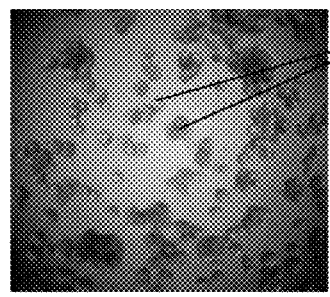
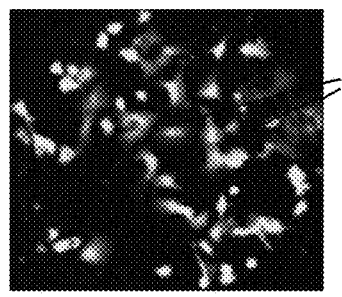
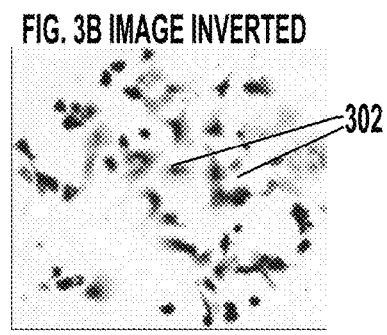
FIG. 3A  FIG. 3B
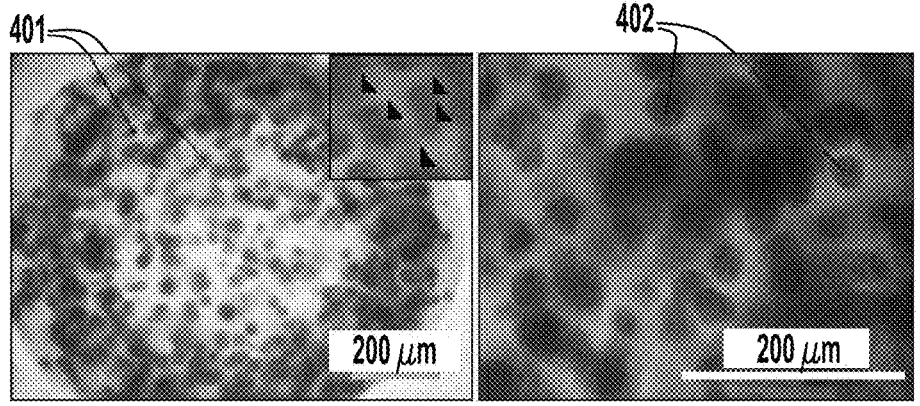
FIG. 4
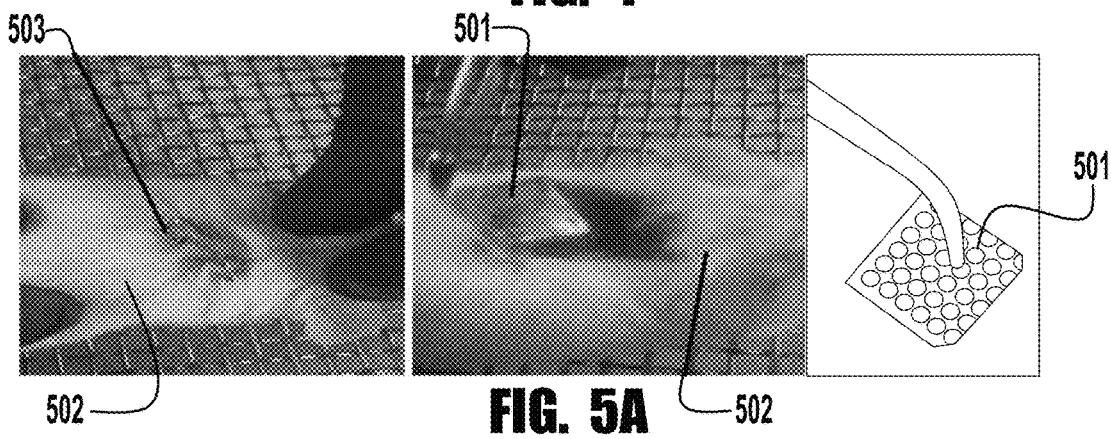
FIG. 5A
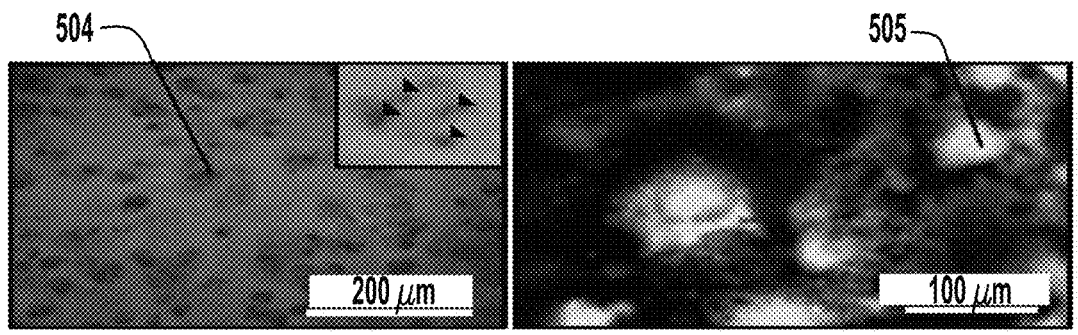
FIG. 5B

FIG. 7B IMAGE INVERTED

3D-PRINTED MINIATURE BIOLOGICAL CONSTRUCTS

This application claims priority to U.S. Provisional Patent Application No. 62/277,592 of Lee, filed on Jan. 12, 2016, entitled "3D-Printed Miniature Biological Constructs," the entire disclosure of which is incorporated by reference.

BACKGROUND

Evaluating the safety of potential therapeutic drugs is a critical component of drug-development. This includes understanding the effects a drug may have on a disease and tissue while in a living organism. The ability to accurately predict hepatotoxicity, neurotoxicity, and cardiotoxicity of compounds in vivo is of particular importance because the liver, brain, and heart are the most important organs that can be adversely affected by chemicals. Thus, for potential human drug candidates in particular, it is useful to simulate a drug's in vivo affects in vitro. In other words, it is valuable to evaluate the drug's safety in vitro on human tissue constructs that can closely mimic the corresponding human tissues and systematically simulate diseases in vivo. However, the current technology is limited in that regard.

Current in vitro options are based on two-dimensional (2D) cell monolayers, three-dimensional (3D) cell spheroids, and 3D bioprinting. Assays based either on 2D cell monolayers or 3D cell spheroids do not adequately mimic the in vivo environment, which limits the quality of information available at the preclinical and clinical states of safety assessment. On the other hand, 3D bioprinting—which utilizes robotic liquid dispensing of human cells layer-by-layer in hydrogels—offers in vitro testing which more accurately mimics the in vivo environment. Yet, this technology is limited by the relatively large scale of tissue constructs and the low throughput of tissue construction and testing. In short, the large tissue constructs are difficult to image and difficult to test in large quantities in a short period of time.

SUMMARY

The present invention is directed to a method for creating miniature multicellular biological constructs that accurately mimic an in vivo environment that may be used in high throughput testing. The method comprises suspending cells in a hydrogel to form a cell suspension, depositing the cell-suspension into a microwell, gelling the cell-suspension, and incubating the cell-suspension to grow the cells into a miniature multicellular biological construct.

The cell-suspension may be deposited into the microwell using a microarray spotter. In some exemplary embodiments more than one cell-suspensions may be deposited into the microwell layer-by-layer. In some further exemplary embodiments, the multiple cell-suspensions may be chosen to mimic a human tissue. The cell-suspensions may then be incubated in vitro or in vivo.

The present invention is further directed to a method of studying cellular and molecular mechanisms comprising suspending cells in a hydrogel to form a cell-suspension, depositing the cell-suspension into a microwell, gelling the cell-suspension, incubating the gelled cell-suspension to grow the cells into a miniature multicellular biological construct, and imaging the miniature multicellular biological construct.

In some exemplary embodiments, the miniature multicellular biological construct may be imaged at varying depths.

BRIEF DESCRIPTION OF THE DRAWINGS

FIGS. 3A and 3B are images of stained hepatocytes. FIG. 3A is an image of stained hepatocytes before irradiation and FIG. 3B is an image of stained hepatocytes after irradiation. This image in FIG. 3B is also shown with the color inverted for clarity.

FIG. 4 is two images of stained Hep3B human hepatoma cells. The image on the left is of Hep3B human hepatoma cells stained with hematoxylin and eosin. The image on the right is of Hep3B human hepatoma cells stained with crystal violet.

FIG. 5A is images of a microwell chip implanted in an NOD SCID gamma mouse and a drawing of the implanted microwell chip. FIG. 5B is images of stained mini-bioconstructs showing viable cell spheroids. The image on the left is of cell spheroids stained with crystal violet. The image on the right is of cell spheroids stained with calcein AM and ethidium homodimer.

DETAILED DESCRIPTION

Figure 1:
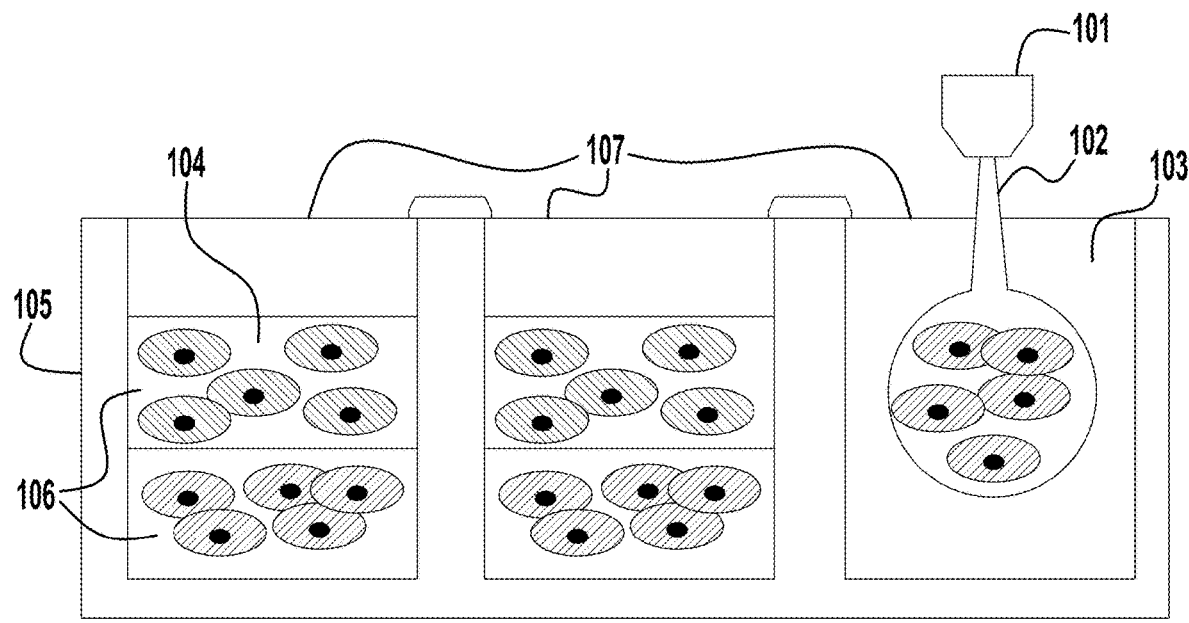
FIG. 1 is a cross-sectional view of an exemplary embodiment of a microwell chip containing cell suspensions and a microarray spotter dispensing cells into an exemplary microwell.
Figure 2:
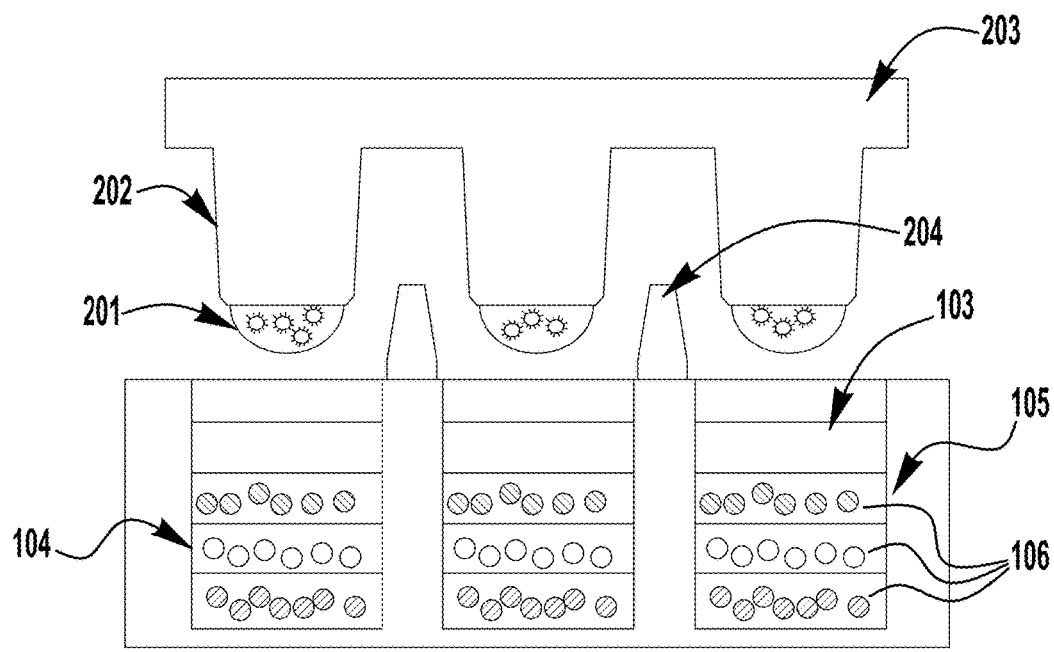
FIG. 2 is a cross-sectional view of an exemplary embodiment of a microwell chip containing cell suspensions and an exemplary embodiment of a micropillar chip containing biosamples.

While various exemplary methods are described herein, other methods and materials similar or equivalent to those described herein are encompassed by the general inventive concepts. All references cited herein, including published or corresponding U.S. or foreign patent applications, issued U.S. or foreign patents, and any other references, are each incorporated herein by reference in their entireties, including all data, tables, figures, and text presented in the cited references.

Unless defined otherwise, all technical and scientific terms used herein have the same meaning as commonly understood by one of ordinary skill in the art to which the invention belongs.

All percentages, parts, and ratios as used herein are by weight of the total formulation, unless otherwise specified. All such weights as they pertain to listed ingredients are based on the active level and, therefore, do not include solvents or by-products that may be included in commercially available materials, unless otherwise specified.

All references to singular characteristics or limitations of the present disclosure shall include the corresponding plural characteristic or limitation, and vice versa, unless otherwise specified or clearly implied to the contrary by the context in which the reference is made.

The methods of the present disclosure can comprise, consist of, or consist essentially of the essential elements of the disclosure as described herein, as well as any additional or optional element described herein or which is otherwise useful in carrying out the general inventive concepts.

To the extent that the terms "includes," "including," "contains," or "containing" are used in the specification or the claims, they are intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

All combinations of method or process steps as used herein can be performed in any order, unless otherwise specified or clearly implied to the contrary by the context in which the referenced combination is made.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, and 10) contained within the range.

The general inventive concepts are directed to a method for creating miniature multicellular biological constructs ("mini-bioconstructs"), and a method utilizing mini-bioconstructs for analyzing cellular and molecular mechanisms.

The inventive method described herein generally includes dispensing cells [102] into a microwell [103] ("printing") using a microarray spotter [101] and incubating the cells to create a desired mini-bioconstruct. In some exemplary embodiments, the mini-bioconstructs may be created to mimic particular tissues such as, but not limited to, a heart, liver, or brain.

A microwell [103], as used in this invention, is a miniscule reservoir. In some exemplary embodiments, the microwell [103] is from about 0.3 mm in width, about 0.3 mm in length, and about 0.3 mm in height to about 2 mm in width, about 2 mm in length, and about 2 mm in height. In some further exemplary embodiments, the microwell [103] may be from about 0.3 mm in diameter and 0.3 mm in height to about 2 mm in diameter and about 2 mm in height. In some further exemplary embodiments, the microwell [103] is about 1.2 mm in diameter and about 1.5 mm in height. The microwell volume may be from about 30 nL to about 8 µL.

The microwell [103] may be housed on a microwell chip [105] that contains an array of microwells [107]. For example, a microwell chip [105] may contain an array of up to about 5,000 microwells. In some exemplary embodiments, the microwell chip [105] may contain about 500 to about 600 microwells. In some exemplary embodiments, the microwell chip [105] may be from about 75 by 25 mm to 128 by 86 mm. The microwell chip [105] may be made of a biocompatible polymer. The biocompatible polymer may be clear or opaque depending on the type of analysis to be performed. For example, in some exemplary embodiments, the microwell chip may be made of clear polystyrene or polydimethylsiloxane (PDMS). Examples of microwell chips include the S+ Microwell Chip made by Samsung Electro Mechanics, Co. and the MBD-W532A made by MBD Korea Co., Ltd.

If the microwell [103] is made of a hydrophobic polymer, it may need to be treated so that it is hydrophilic. Accurately printing [102] biological samples into a small, hydrophobic microwell [103] is challenging due to high surface tension and associated problems such as air bubble entrapment. If the microwell [103] is hydrophobic, air-bubble entrapment may be exacerbated. Air bubble entrapment may further be a problem at the incubating step of this method. To alleviate this problem, the surface property of the microwell [103] may be changed from hydrophobic to hydrophilic. In some exemplary methods, this is carried out by treating the microwell [103] with plasma for 5-30 minutes. Exemplary gases for plasma treatment may be atmospheric air, argon, oxygen, or nitrogen. In addition, in some exemplary embodiments, the surface of the microwell may be coated with a hydrophilic polymer, such as polyethylene glycol, collagen, or poly-L-lysine to enhance the hydrophilicity of the microwell surface.

Before printing [102] cells into the microwell [103], a cell-suspension [104] may be made comprising the cells, at least one hydrogel, and growth media. Optionally, one or more biomolecules, drugs, DNAs, RNAs, proteins, bacteria, viruses, or combinations thereof may be included in the cell-suspension [104]. A hydrogel is generally a polymer that contains water. For example, suitable hydrogels may be alginate, methacrylated alginate, chitosan, hyaluronic acid, fibrinogen, collagen, methacrylated collagen, PuraMatrix, Matrigel, PepGel, and polyethylene glycol. Growth media is generally a liquid designed to support cell growth. Suitable examples of growth media may include Dulbecco's Modified Eagle Medium (DMEM), Roswell Park Memorial Institute medium (RPMI), and William's E. Biomolecules may include molecules that support cellular or tissue growth, such as extracellular matrices (ECMs), growth factors, and carbohydrates. Biomolecules may also include any molecules chosen to mimic a particular biological environment, such as a particular tissue (liver, heart, brain, etc.). The cell concentration of the cell-suspension [104] may be from about 10,000 to about 20 million cells/mL, about 500,000 to about 5 million cells/mL, or about 1 million to about 2 million cells/mL. The growth media may be from about 90 w/v % to about 99.9 w/v % of the final cell-suspension [104]. The hydrogel may be from about 0.1 w/v % to about 10 w/v % of the final cell-suspension [104].

The cells may be stained or otherwise prepared to facilitate imaging, including high-content imaging, before or after the cell-suspension is made. For example, the cells may be stained with fluorescent dyes that indicate certain cellular processes. Examples of dyes and the cellular processes that they may indicate are known in the art, including calcein AM and ethidium homodimer-1 for cell viability and cytotoxicity; Hoechst 33342 for changes in nuclear function; YO-PRO-1/propidium iodide for apoptosis or necrosis; tetramethyl rhodamine methyl ester (TMRM) for mitochondrial membrane potential; fluo-4 AM for intracellular calcium levels; and monochlorobimane (MCB) and thiol green dye for glutathione levels. Cells may also be stained with recombinant viruses carrying genes for various fluorescent biomarkers. Exemplary recombinant viruses are baculoviruses, for example Bac-to-Bac® baculovirus expression system from ThermoFisher. Other suitable staining methods may be known in the art. Examples of fluorescent biomarkers include blue fluorescent protein (BFP), green fluorescent protein (EGFP), orange fluorescent protein (mOrange), or red fluorescent protein (mCherry).

In some exemplary embodiments, more than one cell-type, may be printed [102] into the microwell [103]. The cell-types may be chosen based on the nature of the particular mini-bioconstruct being created or the biological environment being mimicked. If more than one cell-type is to be printed into the microwell, a cell-suspension [104] for each cell-type may be created or several cell-types may be mixed in the same cell-suspension, depending on the nature of the mini-bioconstruct being created. In some exemplary embodiments, more than one type of cell-suspension may be printed layer-by-layer into the microwell depending on the particular mini-bioconstruct being created or the biological environment being mimicked [106]. For example, cell-suspensions may differ depending on variables such as, but not limited to, cell-type, growth factors, extracellular matrices, biomolecules, drugs, DNAs, RNAs, viruses, bacteria, growth media, hydrogels, or combinations thereof.

The microwell [103] may be preconditioned before printing the cell-suspension into the microwell by printing DNAs, RNAs, growth media, biopolymers, growth factors, extracellular matrices, biomolecules, drugs, proteins, viruses, bacteria, hydrogels, cross-linking agents, or combinations thereof into the microwell. To avoid clogging, gelling hydrogels may be done in more than one step. For example, first, a crosslinking agent may be printed into the microwell [103] and, second, a hydrogel containing cells may then be printed into the microwell already containing the crosslinking agent so that a gel is formed. Cross-linking agents may include salts or enzymes that facilitate gelling of the hydrogel. Examples of suitable cross-linking mechanisms include ionic crosslinking (e.g., alginate with barium chloride and calcium chloride; PuraMatrix with salts), affinity/covalent bonding (e.g., functionalized polymers with streptavidin and biotin), photopolymerization (e.g., methacrylated alginate with photoinitiators), and biocatalysis (e.g., fibrinogen with thrombin).

In some exemplary embodiments, the cell suspension [104] may be printed [102] by a microarray spotter [101] into the microwell [103]. A microarray spotter [101] is a robotic liquid dispensing system capable of printing small amounts of biological samples, also known as "spots," into a microwell [103] ("printing"). In some exemplary embodiments, the microarray spotter [101] may be capable of printing [102] spots into multiple microwells [107] on the same microwell chip [105] to facilitate high-throughput testing. The microarray spotter [101] may be capable of printing from about 20 nL to about 3 µL of cell-suspension [104] into the microwells [103]. Exemplary microarray spotters include S+ Microarrayer, commercially available from Samsung and MicroSys, PixSys, and CellJet, commercially available from DigiLab.

In some exemplary embodiments, more than one layer of cells may be printed into the microwell. In some further exemplary embodiments, each layer of cells in the microwell comprises different cell-types [106]. In some further exemplary embodiments, the number of layers and different cell-types are chosen to create a mini-bioconstruct that mimics a particular tissue or biological environment. For example, in some exemplary embodiments the number of layers and different cell-types may be chosen to mimic a tissue such as, but not limited to, a heart, liver, or brain. For example, human liver tissue constructs may be created by printing primary hepatocytes/HepaRG, hepatic sinusoidal endothelial cells, hepatic stellate cells, and Kupffer cells layer by layer in photocrosslinkable collagen to maintain liver-specific functions.

In some exemplary embodiments, after the cell-suspension [104] is printed [102] into the microwell [103], it may be gelled. For example, the cell-suspension may be cross-linked using a suitable mechanism explained above.

After being gelled, the cell-suspension may be incubated to grow the cells into a mini-bioconstruct. Incubation may be carried out in vitro or in vivo.

In some exemplary embodiments, the cell suspension [104] may be incubated in vitro. For example, the microwell [103] may be submerged in growth media. Suitable growth media include Dulbecco's Modified Eagle Medium (DMEM), Roswell Park Memorial Institute medium (RPMI), and William's E. In some further exemplary embodiments, the bottom of the microwell [103] may be a permeable membrane, which may enhance diffusion of the growth media through the layers of cells [106] in the microwell.

In some exemplary embodiments, the cell suspension [104] may be incubated in vivo. For example, the microwell [103] may be implanted into a living organism (see, e.g., FIG. 5A). In some exemplary embodiments, a microwell [103] may be implanted under an animal's skin. The animal may be immunodeficient so that the microwell [103] and its contents do not cause an immune response in the animal.

In some exemplary embodiments at least one biosample [201] may be added to the mini-bioconstruct. Suitable biosamples [201] may include biomolecules, drugs, DNAs, RNAs, cells, growth factors, extracellular matrices, proteins, viruses, bacteria, or combinations thereof. The at least one biosample [201] may be chosen to mimic a particular biological environment or disease. In some exemplary embodiments, the at least one biosample [201] may be printed directly into the mini-bioconstruct using the microarray spotter. In some further exemplary embodiments, the at least one biosample [201] may be printed onto a micropillar [202] using a microarray spotter [101], and the micropillar may subsequently be inserted into the microwell [103] containing the mini-bioconstruct [104].

A micropillar [202] may be housed on a micropillar chip [203] that contains more than one micropillar. The micropillar's size corresponds to the size of the microwell [103] so that it may fit inside the microwell. In some exemplary embodiments, the microwell chip includes spacers [204] in between the microwells [103] to control the depth at which the micropillars [202] are inserted into the microwells [103]. In some exemplary embodiments, about 100 pL to about 100 nL of at least one biosample may be printed onto a micropillar [202].

The mini-bioconstruct may be examined by imaging the cells. For example, the mini-bioconstruct may be stained with fluorescent dyes (e.g., calcein AM, ethidium homodimer-1, Hoechst 33342, YO-PRO-1, propidium iodide, TMRM, fluo-4 AM, MCB, a thiol green dye), antibodies with fluorescent tags (e.g., Tyramide signal amplification kit), or recombinant viruses carrying genes for biomarkers (e.g., Bac-to-Bac® baculovirus system from ThermoFisher). In some exemplary embodiments, the mini-bioconstruct may be imaged using a high-content imaging scanner. Suitable imaging devices include the S+ Scanner, commercially available from Samsung, GenePix Scanner, commercially available from Molecular Devices, and Cellomics Arrayscan, commercially available from ThermoFisher. In some further exemplary embodiments, the various layers of cells are individually targeted for imaging using different Z-focus positions. The small size of the mini-bioconstruct allows for imaging at different Z-focus positions.

By using microwell chips containing an array of microwells—sometimes hundreds on one chip—the methods described herein may be used in high-throughput, high-content, 3D cell-imaging assays. The mini-bioconstructs create an in vivo-like environment in which accurate pre-clinical and clinical drug-safety testing may be performed. Further, the small-scale of the mini-bioconstructs allows for high-content imaging throughout the several layers of the mini-bioconstruct and high-throughput testing. Hundreds of settings may be tested in hundreds of mini-bioconstructs on a single chip using this method.

Example 1

FIGS. 3A and 3B are referenced in Example 1. It has been demonstrated that primary mouse hepatocytes may be printed in photocrosslinkable alginate into a microwell and exposed to long wavelength ultraviolet (UV) light while maintaining high cell viability. A 1:1:1 cell suspension was prepared using primary mouse hepatocytes, 12% oxidized methacrylated alginate (OMA), and 0.15% photoinitiator (PI) solution, for a concentration of 2 million cells/mL. The cell-suspension was printed into a microwell chip and irradiated with UV light for 3 minutes to gel the cell-suspension. The gelled cell-suspension was incubated for four days in vitro, creating a liver-like mini-bioconstruct. The hepatocytes were then stained with calcein AM and ethidium homodimer-1 to measure cell viability. The cells within the mini-bioconstruct were imaged using the S+ Scanner for high-content analysis. As displayed in FIGS. 3A and 3B, the cells maintained high viability even after three minutes of irradiation with long wavelength UV light. The stained, post-radiation hepatocytes [302] appear similar in quantity to the printed hepatocytes [301] prior to staining and irradiation.

Example 2

FIG. 4 is referenced in Example 2. It has also been demonstrated that Hep3B human hepatoma cells may be printed in photocrosslinkable alginate into a microwell chip and exposed to long wavelength UV light while maintaining high cell viability. 640 nL of Hep3B cells in alginate were printed into a microwell and incubated in a petri dish containing RPMI for 6 days to observe appropriate morphology change and spheroid formation over time. The cells were stained using hematoxylin and eosin (H & E) staining (FIG. 4, left) and crystal violet staining (FIG. 4, right) to visualize the nucleus and cytoplasm in cell spheroids [401, 402]. As shown in FIG. 4, a significant number of viable cell spheroids were detected using H & E staining [401] and crystal violet staining [402].

Example 3

FIGS. 5A and 5B are referenced in Example 3. In addition to incubating the mini-bioconstructs in vitro, they may also be incubated in vivo by implanting the microwell chip in animals. For example, to investigate optimum microenvironments for tissue regeneration and create human mini-bioconstructs in vivo, 640 nL of Hep3B cells in alginate were printed in multiple microwells on a microwell chip (1×1 cm$^2$) [501] representing four different microenvironments. The chip was implanted subcutaneously near the shoulder blades in an NOD SCID gamma mouse [502]. A staple [503] was used to prevent the wound from opening during incubation. The cells in the microwell chip [501] were incubated for two weeks in the mouse [502]. The chip was then recovered from the mouse [502] and the mini-bioconstructs were stained using crystal violet (FIG. 5B, left) and calcein AM and ethidium homodimer (FIG. 5B, right) to demonstrate the formation of viable spheroids [504, 505]. As shown in FIG. 5B, a significant number of viable cell spheroids were detected using crystal violet [504] and calcein AM and ethidium homodimer staining.

Example 4

Figure 6A:
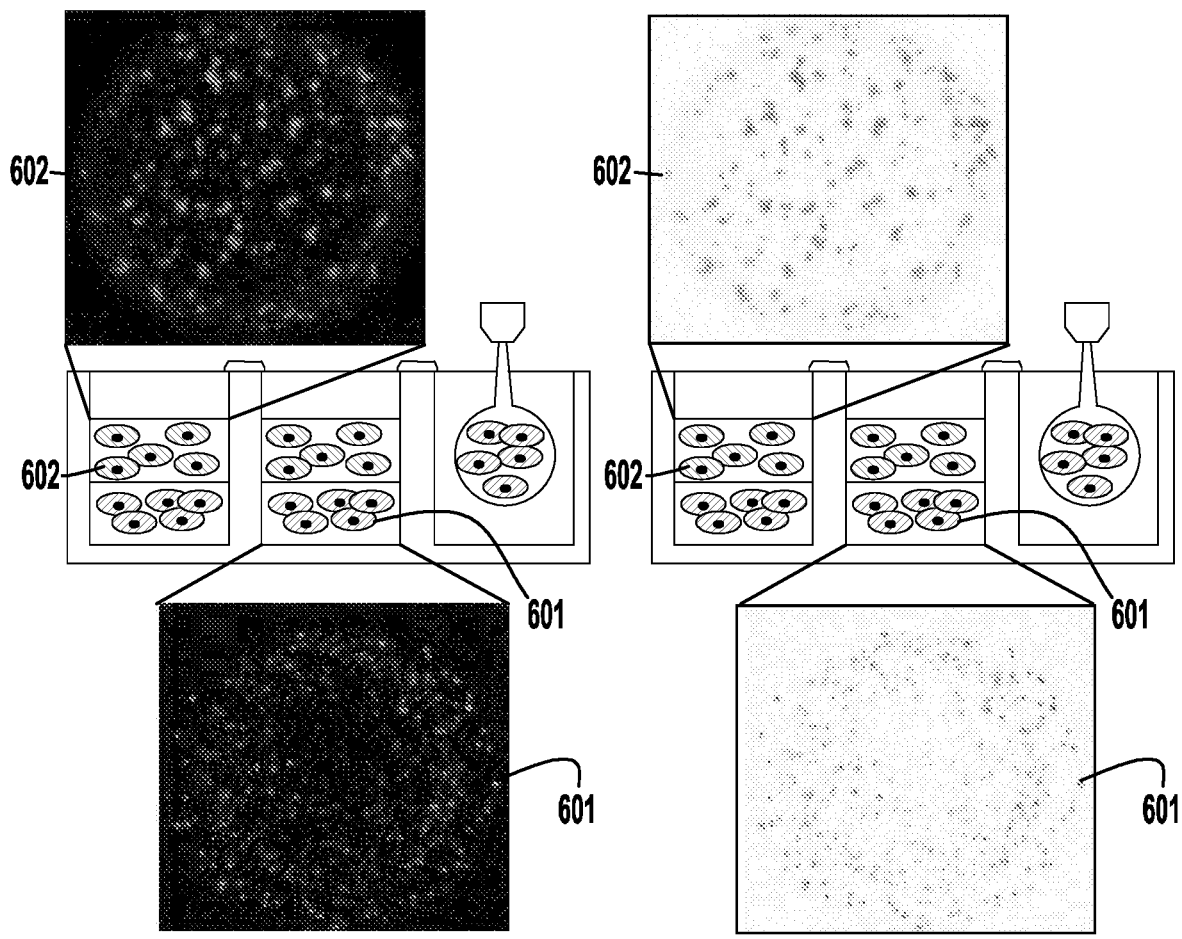
FIG. 6A is a cross-sectional view of an exemplary embodiment of a microwell chip containing layers of red- and blue-stained cells and a microarray spotter dispensing cells into an exemplary microwell and images of the red- and blue-stained cells as described in Example 5. These images are also shown with the color inverted for clarity.

FIG. 6A is referenced in Example 4. It has been demonstrated that cell images are obtainable at different Z-focus positions within the mini-bioconstruct. A microwell chip was prepared by printing 320 nL of 20 mM $BaCl_2$ into a microwell and dried overnight. Monolayers of Hep3B cells in a T-75 flask were stained with a blue fluorescent Hoechst 33342 dye at a concentration of 25 µM for one hour. The Hoechst 33342-stained cells were then detached from the flask with trypsin, and cell pellets were prepared by centrifugation.

A cell-suspension was prepared by mixing the Hoechst 33342-stained cells with fresh growth media and alginate for a final cell concentration of 1.5 million cells/mL and 0.75 w/v % of alginate [601].

Different Hep3B cells were stained red with 0.5 µM tetramethyl rhodamine methyl ester (TMRM). The TMRM-stained cells were similarly prepared in a cell-suspension containing growth media and alginate [602].

320 nL of the blue Hoechst 33342 cell-suspension [601] was first printed into the microwell, and then 320 nL of the red TMRM cell-suspension [602] was printed on top in the same microwell. The bottom layer of Hoechst 33342 cell-suspension [601], thus, occupied about 300 µm in height and the upper layer of TMRM cell-suspension [602], thus, occupied about 300 µm in height. The microwell was immediately sealed with a gas-permeable membrane to avoid water evaporation.

Five fluorescent images were taken using the S+ scanner from five different Z-axis positions. The distance between the Z-axis positions was approximately 100 µm in height. As shown in Table 1, the red TMRM-stained cells were detectable at two Z-axis positions corresponding to the upper layer of the microwell and the blue Hoechst 33342-stained cells were detectable at three Z-axis positions corresponding to the lower layer of the microwell.

TABLE 1

| Z-Axis Height | Cell Image Color |
|---|---|
| ~500 µm | Red |
| ~400 µm | Red |
| ~300 µm | Blue |
| ~200 µm | Blue |
| ~100 µm | Blue |

Example 5

Figure 6B:
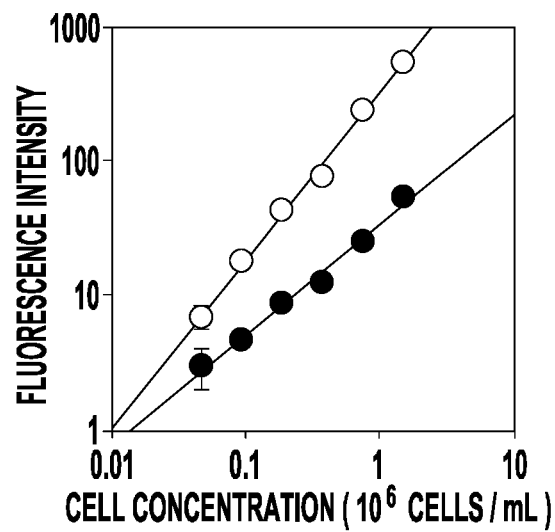
FIG. 6B is a table demonstrating the fluorescent intensity versus the number of cells in the layers described in Example 5.

FIGS. 6A and 6B are referenced in Example 5. In addition to successfully demonstrating that cell images are obtainable from two different alginate layers containing red-[602] and blue-[601] stained Hep3B cells in a microwell chip, it has also been demonstrated that the number of cells printed can be accurately quantified by measuring fluorescent intensity of the cells in two layers.

320 nL of 150 μg/mL collagen I was printed in a microwell and dried overnight, followed by 320 nL of 20 mM $BaCl_2$ being printed in the microwell and dried overnight. Then 320 nL of Hoechst 33342-stained cells at six different concentrations (0.047-1.5 million cells/mL with 2-fold serial dilution) were printed in six different regions of the microwell. TMRM-stained cells at six different concentrations (0.047-1.5 million cells/mL with 2-fold serial dilution) were printed on top of the Hoechst 33342-stained cell layers. The microwell was sealed with a gas-permeable membrane immediately after printing.

Cell images were obtained of the two cell layers using the S+ scanner. FIG. 6B contains a graph that represents the change of fluorescent intensity from Hoechst 33342 (○)- and TMRM (●)-stained Hep3B cells at different seeding densities.

As demonstrated in FIG. 6B, the fluorescent intensity was linearly proportional to the number of cells in the layers.

Example 6

Figure 7A:
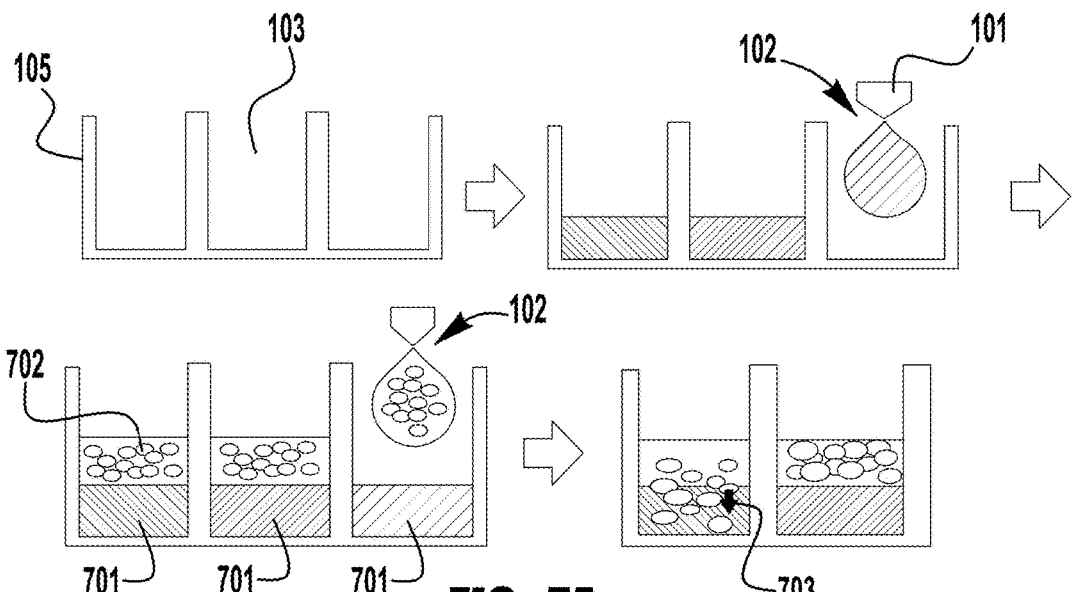
FIG. 7A is a cross-sectional view of an exemplary embodiment of a microwell chip containing chemoattractant mixtures (and a microarray spotter dispensing a chemoattractant mixture) and Hep3B cells as described in Example 6.
Figure 7B:
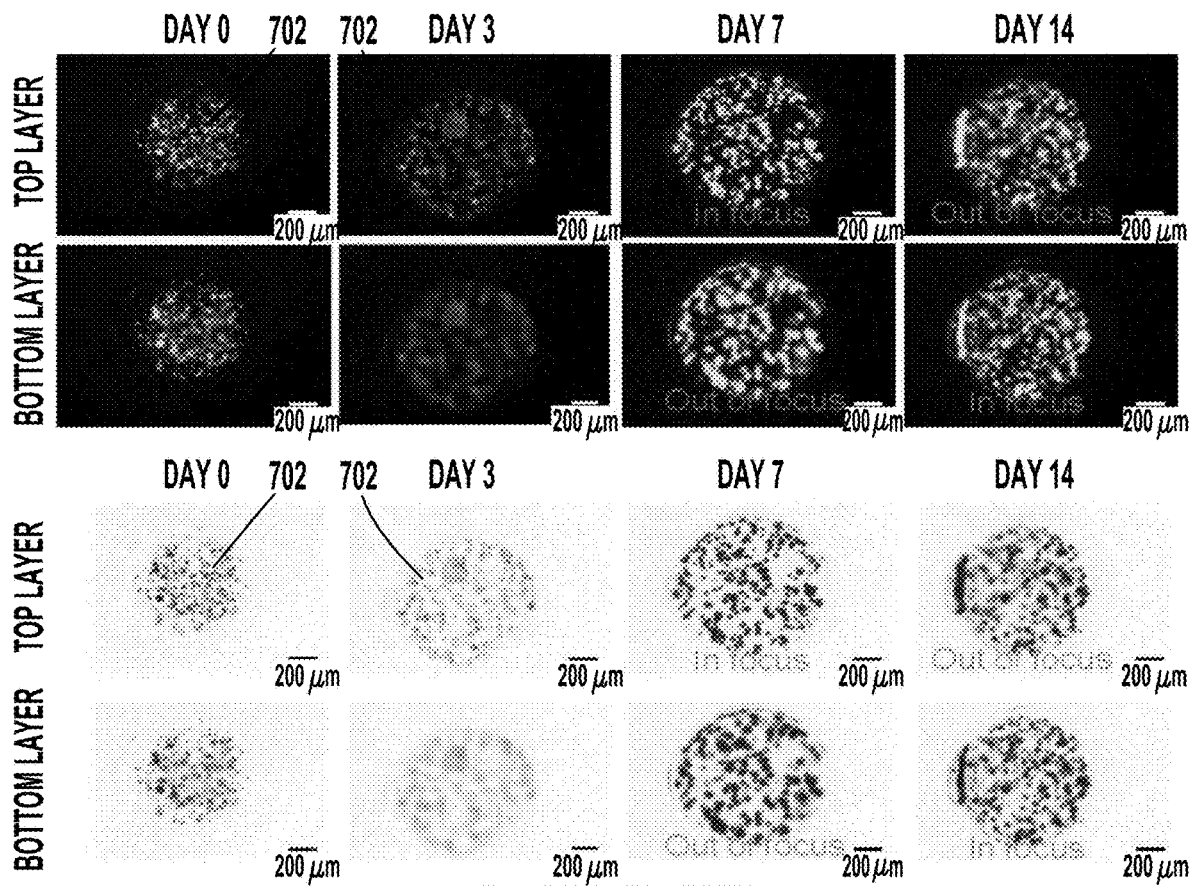
FIG. 7B is images of Hep3B cells stained with calcein AM and ethidium homodimer as described in Example 6. These images are also shown with the color inverted for clarity.

FIGS. 7A and 7B are referenced in Example 6. It has also been demonstrated that mini-bioconstructs may be used to mimic tumor-like spheroids to study cancer cell migration behavior. For example, cancerous cells may be printed [102] on top of one or several types of chemoattractants [701] in microwells [103] on a microwell plate [105]. The mini-bioconstructs may then be stained, incubated, and then imaged to analyze how a chemoattractant may affect a cancer cell migration [703].

In Example 6, a model chemoattractant (1.5 mg/mL Matrigel) was mixed with a photocrosslinkable hydrogel (2 w/v % OMA) [701]. The chemoattractant mixture [701] was then printed at the bottom of a number of microwells [103] on a microwell chip [105]. The mixture was polymerized with near-UV light in the presence of photoinitiators. Hep3B human hepatoma cells were mixed with a photocrosslinkable hydrogel (2 w/v % OMA) [702] and printed on top of the chemoattractant mixture [701], polymerized with near-UV light in the presence of photoinitators, and incubated for two weeks.

The mini-bioconstructs were then stained with calcein AM and ethidium homodimer and imaged to determine Hep3B cell [702] migration [703] into the chemoattractant mixture [701]. Migration was determined by acquiring images of Hep3B cells [702] throughout the mini-bioconstruct and determining which layer the Hep3B cells were in by analyzing in-focus and out-of-focus images of Hep3B cells using ImageJ (Fourier transform analysis for detecting image blurriness) (FIG. 7B). The scale bar in the images in FIG. 7B is 200 μm. As shown in FIG. 7B, by day 14, Hep3B cells [702] were seen in focus in the bottom layer, meaning that the cells had migrated to the bottom layer containing the chemoattractant mixture [701].

While the present application has been illustrated by the description of embodiments thereof, and while the embodiments have been described in considerable detail, it is not the intention of the Applicant to restrict or in any way limit the scope of the appended claims to such detail. Additional advantages and modifications will readily appear to those skilled in the art. Therefore, the application, in its broader aspects, is not limited to the specific details, the representative compositions or formulations, and illustrative examples shown and described. Accordingly, departures may be made from such details without departing from the spirit or scope of the general disclosure described herein.

I claim:

1. A method for studying cellular and molecular mechanisms comprising:
    (a) treating the surface of a microwell to make it hydrophilic;
    (b) depositing a layer of a chemoattractant into the bottom of the microwell;
    (c) depositing 8 μl or less of a cell-suspension containing cancer cells into the microwell on top of the layer of chemoattractant;
    (d) gelling the cell-suspension; and
    (e) incubating the microwell for one week or more; and
    (f) imaging the different layers of the cell-suspension and chemoattractant to determine migration of the cancer cells.

2. The method of claim 1 wherein the cell-suspension is deposited into the microwell using a microarray spotter.

3. The method of claim 1 wherein at least one biosample is dispensed into the cell-suspension.

4. The method of claim 1 wherein the cell-suspension and chemoattractant are imaged at varying depths.

5. The method of claim 1 wherein more than one cell-suspension is made and deposited into the microwell.

6. The method of claim 5 wherein the differing cell-suspensions are chosen to mimic a human tissue.

7. The method of claim 1 wherein more than one cancer cell type is deposited into a microwell chip containing multiple microwells.

* * * * *